United States Patent [19]
Summer et al.

[11] Patent Number: 5,989,023
[45] Date of Patent: Nov. 23, 1999

[54] INTRAORAL JAW TRACKING DEVICE

[75] Inventors: John D. Summer, 9601 NW. Leahy Rd. #305, Portland, Oreg. 97229; Erik Bodegom, Portland, Oreg.; Allen Lee, Portland, Oreg.

[73] Assignee: John D. Summer, Portland, Oreg.

[21] Appl. No.: 09/224,186

[22] Filed: Dec. 31, 1998

[51] Int. Cl.[6] .................................................. A61C 19/04
[52] U.S. Cl. ........................................................... 433/69
[58] Field of Search ................................ 433/6, 69, 215; 607/135

[56] References Cited

U.S. PATENT DOCUMENTS

| | | | |
|---|---|---|---|
| 4,014,097 | 3/1977 | Pameijer | 32/20 |
| 4,204,326 | 5/1980 | Dimeff | 433/50 |
| 4,303,077 | 12/1981 | Lewin et al. | 128/777 |
| 4,303,919 | 12/1981 | Dimeff | 340/870.37 |
| 4,330,276 | 5/1982 | Becker et al. | 433/69 |
| 4,386,405 | 5/1983 | Lewin et al. | 364/415 |
| 4,447,207 | 5/1984 | Kataoka et al. | 433/69 |
| 4,495,952 | 1/1985 | Klett | 128/777 |
| 4,639,220 | 1/1987 | Nara et al. | 433/69 |
| 4,765,345 | 8/1988 | Adib | 128/777 |
| 4,788,987 | 12/1988 | Nickel | 128/777 |
| 4,836,778 | 6/1989 | Baumrind et al. | 433/69 |
| 4,837,685 | 6/1989 | Jokela | 364/413.02 |
| 4,859,181 | 8/1989 | Neumeyer | 433/69 |
| 5,143,086 | 9/1992 | Duret et al. | 128/777 |
| 5,340,309 | 8/1994 | Robertson | 433/69 |
| 5,588,430 | 12/1996 | Bova et al. | 128/653.1 |

OTHER PUBLICATIONS

Watt, David M.; Gnathosonic Diagnostics and Occlusal Dynamics; Praeger Publishers, New York, NY., 1981; pp. 30–31.

"A New Method for Recording Mandibular Position During Nocturnal Bruxism," by Y. Akamatsu, S. Minagi & T. Sato, Journal of Oral Rehabilitation 1996 23; pp. 622–626.

*Primary Examiner*—Nicholas D. Lucchesi
*Attorney, Agent, or Firm*—Marger Johnson & McCollom, PC

[57] ABSTRACT

A jaw tracking device, which fits entirely in the mouth and can be attached to conventional removable dental appliances, tracks the location and movement of the lower jaw with high precision and speed when the mouth is closed or nearly closed by recording the projection of light from a light emitting diode, laser diode, or fiberoptic source fixed to the lower dental arch onto one or two position sensitive detectors (PSDS) fixed to the upper dental arch. Since the system acquires data quickly enough to record the minute deflections of the lower jawbone which occur each time the jaw is closed eccentrically, it can be used with acoustic sensors attached to the individual teeth in order to analyze a person's bite. Since each PSD relies on only four outputs, its data can be easily transmitted by telemetry so that it can be used to track the location of the jaw during sleep without requiring wires protruding from the mouth of the sleeping subject.

21 Claims, 5 Drawing Sheets

INTRAORAL JAW TRACKING DEVICE

BACKGROUND OF THE INVENTION

This invention relates generally to methods and apparatus for detecting alignment of upper and lower teeth and more particularly to methods and apparatus for tracking the movement of the lower jaw relative to the upper jaw. There have been many types of jaw tracking devices developed for use in dentistry. They can generally be categorized as electro-mechanical devices and electro-optical devices.

Of the known prior art electro-optical devices used for jaw tracking, many employ reference points, either visually identifiable points or light emitting diodes, carried by frameworks attached to both upper and lower jaws and viewed by an externally mounted video camera. Most prior art electro-optical devices employ light emitting diodes carried by frameworks attached to the lower jaw and a video camera or other light sensing means attached to the head or upper jaw.

One problem with prior art electro-optical jaw tracking devices is that the frameworks by which the components are attached to the jaw or jaws must be custom fabricated for each patient and tend to interfere with natural jaw movements. The extraoral sensing means may either be attached or unattached to the patient. Unattached devices must be able to sense the positions of extraoral signal generating components or reference points attached to both upper and lower jaws. Attached devices must be attached to the patient's head or upper jaw by a framework affixed to the patient. Frameworks cemented onto the patient's teeth either cover the surfaces of the teeth and thereby alter the bite as well as the jaw movement pattern or must be custom fabricated for each subject in a way that allows them to fit around the teeth so as to avoid interfering with the bite. Such custom fabricated frameworks have been used for research, but they are too difficult to fabricate for routine clinical use. Furthermore, any framework that must extend through the lips interferes to some degree with neuromuscular proprioception and thereby also with natural jaw-movement patterns.

Another problem with prior art jaw tracking devices is that they cannot acquire data rapidly enough to track the minute deflections of the jawbone that are generated by inclined tooth contacts on many jaw closures. In 1980 Dr. David Watt published recordings of jaw tracking using a high speed camera to show that eccentric jaw closing trajectories frequently result in initial tooth contacts on steep inclines, which force the jaw to suddenly alter its direction and slide a fraction of a millimeter toward a more central position where subsequent multiple tooth contacts occur. D. Watt, *Gnathosonic Diagnosis and Occlusal Dynamic*. Furthermore, Dr. Watt showed that, during a single jaw closure, the jaw may change its direction more than once by striking multiple deflective tooth contacts before settling into a stable position. High speed cameras, like the one Watt used, are able to track jaw movements accurately if the lips are kept apart so that the cameras can track a point on an upper and a lower tooth. Keeping the lips apart, however, interferes with natural jaw movements much like frameworks do.

Most of the prior art devices track the movements of the jaw by means of charge coupled devices (CCD). However even a CCD screen cannot be scanned quickly enough to record the multiple rapid shifting of the jaw, which can occur in time frames of 10 to 50 milliseconds after an initial unstable tooth contact and before the final resting of the jawbone in stable interdigitation. Knowing the direction of slide of the jawbone after a deflective initial tooth contact helps determine which area of a tooth was actually hitting prematurely.

Another disadvantage with prior art jaw tracking devices is that they are not designed to be compatible with free head movement. Recently the use of miniature acoustic sensors has been developed to allow dentists to analyze and adjust a patient's bite. These sensors can determine which teeth hit first each time the jaw is closed. But the order of tooth contacts depends on the closing trajectory taken by the jawbone, and that trajectory varies a great deal within an area extending a couple of millimeters around the fully closed and maximally interdigitated jaw position. For example, if the jaw closes slightly to the right of the midline, the teeth on the right are likely to hit before the teeth on the left. In order for the dentist to accumulate enough tooth contact and jaw tracking data to create a map of these tooth contact patterns, known as the occlusal interface, the patient needs to be able to tap the teeth repeatedly while moving the jaw and the head into a wide variety of different postures. The prior art jaw tracking devices employ extraoral frameworks that interfere with the ability of the head and jaw to exhibit a normal and natural range of motion.

Still another disadvantage of all prior art jaw tracking devices is that they cannot be used with telemetry during sleep. Horizontal jaw tracking is needed during sleep to record the jaw positions used for nocturnal bruxism (grinding and clenching of the teeth). Many dentists believe that nocturnal bruxism is a common cause of dental problems. Studies have shown that nocturnal bruxism often occurs with forces that are significantly greater than even maximal voluntary forces while awake. Furthermore, there is evidence that much of nocturnal bruxism occurs in jaw positions that are shifted to the side, forward, or backward from the fully closed and maximally interdigitated jaw position. Knowing the horizontal jaw position in which a person's bruxism occurs allows a dentist to restore the teeth in a manner that can best resist the forces that arise during nocturnal bruxism. None of the prior art jaw tracking devices, however, can be used during sleep because they all employ frameworks that would interfere with sleep. *The Journal of Oral Rehabilitation* 1996 23: 622–626 recently published an account of an effort to record jaw position during sleep by means of a device that employed two magnetic reed switches. But the system of reed switches used was only able to approximate the position of the jaw, because each switch simply produced a signal if the magnet attached to the lower jaw on its side was closer than 2.65 mm from the switch.

Thus, it is an object of this invention to provide a jaw tracking device that is small enough to be located completely in the mouth without the need for any framework that extends through the lips.

It is a further object of this invention to provide a jaw tracking device that acquires data rapidly enough to record the direction of the very small slide of the lower jawbone during the time interval between the first tooth contact and subsequent tooth contacts.

It is a further object of this invention to provide a jaw tracking device that relies on few enough outputs so that they can be transmitted by telemetry during sleep without any need for wires coming out of the mouth.

It is a further object of the invention to provide a jaw tracking device that can be carried on existing removable dental appliances.

SUMMARY OF INVENTION

These objectives are achieved by employing a jaw tracking system that fits entirely in the patient's mouth where it can be mounted on any conventional removable dental appliance. The invention describes a device and method for tracking a person's lower jaw movement. A position sensitive detector (PSD) is mounted on a dental appliance formed to fit one of the person's dental arches. A light source, such as an LED, is mounted on another dental appliance formed to fit the person's other dental arch. The light source is mounted such that it shines light on the center of the detector when the jaw is in its central and maximally interdigitated position. The detector generates electrical data tracking the position of the light on the detector.

The foregoing and other objects, features and advantages of the invention will become more readily apparent from the following detailed description of a preferred embodiment of the invention, which proceeds with reference to the accompanying drawings.

DETAILED DESCRIPTION

Figure 1:
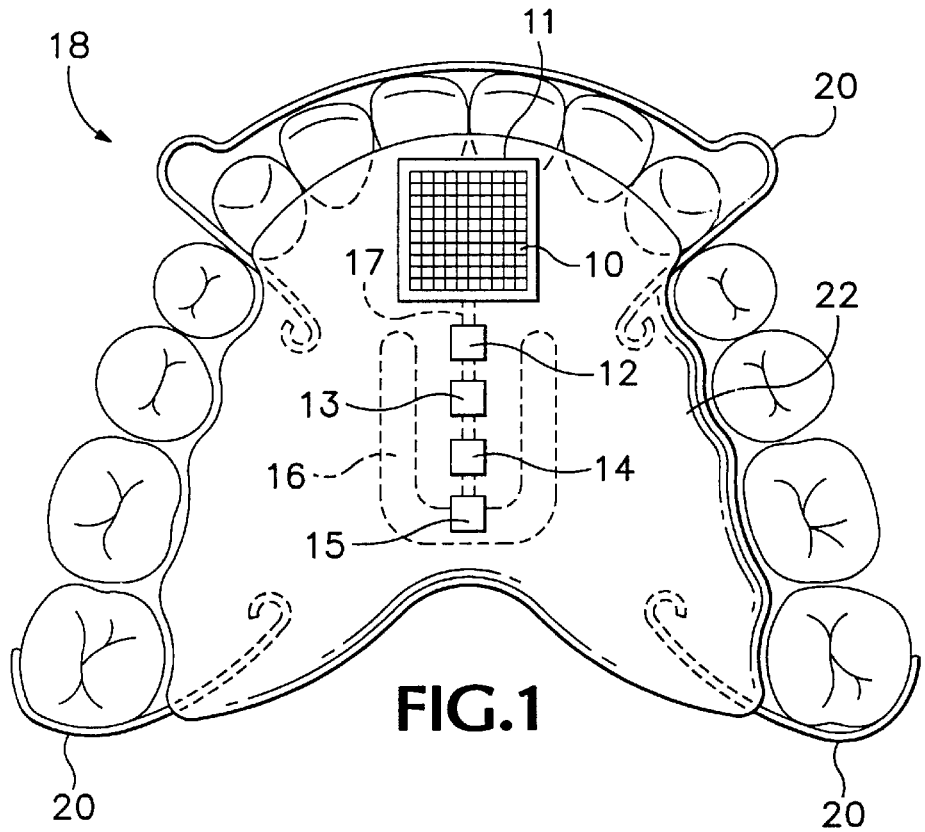
FIG. 1 is a coronal view of the palate and upper dental arch fitted with removable dental appliance holding a two-dimensional position sensitive detector of a jaw tracking device.
Figure 2:
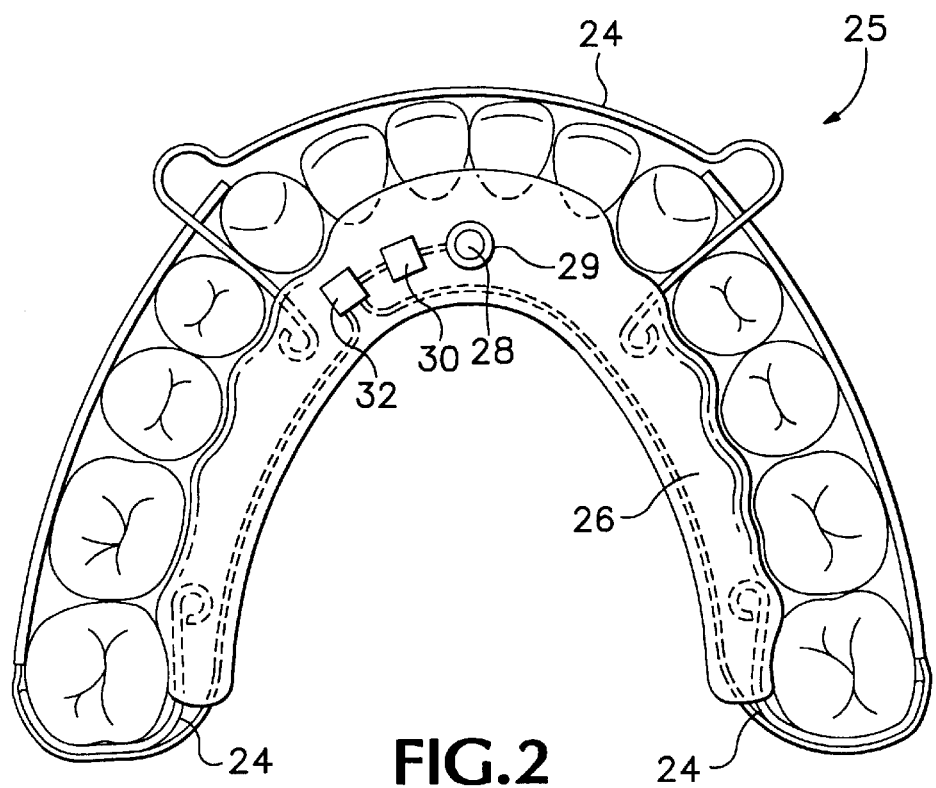
FIG. 2 is a coronal view of the lower dental arch fitted with a removable dental appliance holding a light source of a jaw tracking device.
Figure 3:
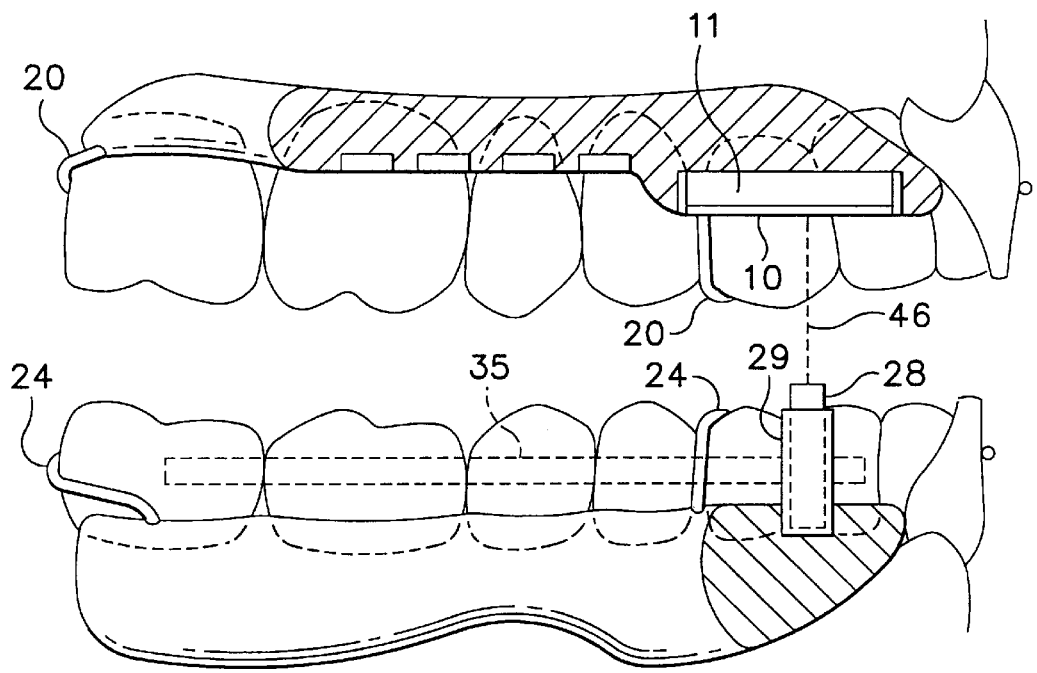
FIG. 3 is a cutaway side view of a partly open mouth with the upper dental appliance of FIG. 1 and the lower dental appliance of FIG. 2.
Figure 4:
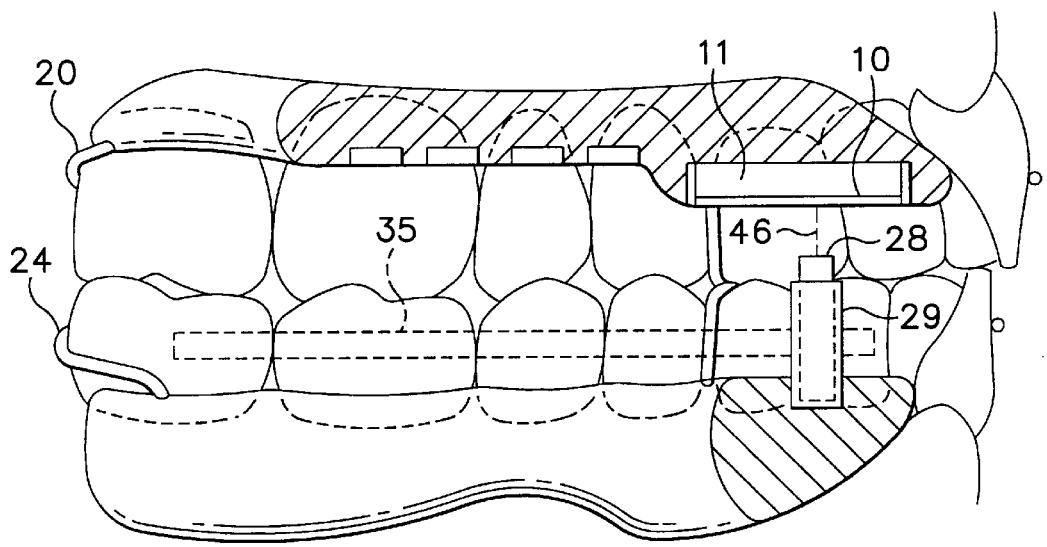
FIG. 4 is a cutaway side view of a closed mouth with the upper dental appliance of FIG. 1 and the lower dental appliance of FIG. 2.

In FIGS. 1, 3 and 4, a two-dimensional position sensitive detector (PSD) 10 comprises a light detector that has a screen measuring approximately 1 cm×1 cm, small enough to be received entirely in the mouth. The PSD 10 has a substantially planar detection surface visible in FIG. 1. The upper dental appliance comprises a molded sheet of acrylic 22 fitted to a model of the patient's upper dental arch 18 much like an orthodontic retainer. The upper dental appliance also comprises holding wires 20 having one end anchored in the acrylic molding 22. The other end of the wires maintain contact with the outer surfaces of the teeth to stabilize the upper dental appliance on the teeth. A PSD holding box 11 is also embedded into the acrylic molding 22. The PSD 10 fits precisely in the PSD holding box 11 and is removable from the PSD holding box 11. The PSD holding box 11 is positioned in the acrylic molding 22 as closely as possible to the back of the lower front teeth, where a light source 28 (in FIGS. 2 and 3) is mounted in a lower dental appliance. The PSD 10 has outputs 17 that are connected to an amplifier 12, a signal conditioning element 13, a power supply 14 and a transmitter 15. An antenna 16 is embedded in the palatal area of the acrylic molding 22. It is foreseen that the antenna 16 may also be mounted on the outside (the cheek side) of the dental arch for transmission to an extra-oral receiver (not shown).

FIG. 2 is a coronal view of a lower dental arch 25 fitted with a lower removable dental appliance holding a light source 28 of a jaw tracking device. The lower dental appliance comprises a molded sheet of acrylic 26 fitted to a model of the patient's lower dental arch 25 much like an orthodontic retainer. The lower dental appliance also comprises holding wires 24 that are anchored in the acrylic molding 26 at one end. The other end of the wires maintain contact with the outer surfaces of the teeth to stabilize the lower dental appliance on the teeth. The light source 28, such as a light emitting diode (LED), fits precisely into and is removable from a light source holder 29, such as a stainless steel tube, embedded in the acrylic molding 26. The light source holder 29 is preferably fitted behind the lower front teeth, but may be fitted in another suitable location depending on the spatial relationship of the patient's upper and lower teeth. Optimally, the LED is powered by a battery 30 mounted on the lower dental appliance. For tests not performed during sleep studies, an external power supply could be used. Since the LED may be used with a battery mounted on the lower dental appliance, the LED should be designed to minimize the current drain on the battery.

In FIG. 3, the upper dental appliance is attached to the upper dental arch and held on by the holding wires 20. The lower dental appliance is attached to the lower dental arch and held on by the holding wires 24. The PSD 10 is set in the PSD holding box 11 in the upper dental appliance. The light source 28 is set in the light source holder 29 in the lower dental appliance and is emitting a light beam 46 toward the PSD 10 of the upper dental appliance. The configuration shown in FIG. 3 is for a patient with a class 1 occlusion. For a patient with a class 2 occlusion, the light source 28 may be positioned on the front of the lower front teeth.

FIG. 4 shows a cutaway side view of a closed mouth with the upper dental appliance of FIG. 1 and the lower dental appliance of FIG. 2. The configuration of the dental appliances shown in FIG. 3 is shown with the mouth closed. The light beam 46 projects onto the PSD 10. This figure demonstrates the close alignment and central orientation of the light source 28 and the PSD 10. By ensuring that the light beam 46 hits the center of the PSD and that the light source 28 and the PSD 10 are as close as possible when the mouth is fully closed, the PSD 10 can be designed to be no larger in area than necessary.

Figure 5:
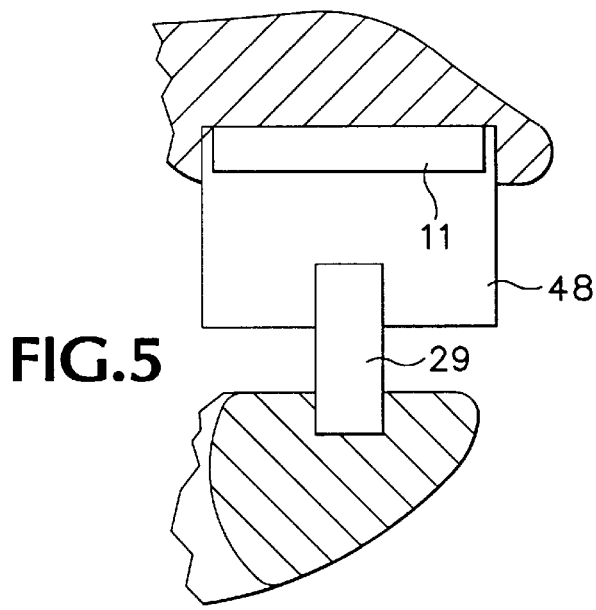
FIG. 5 is a device for creating the dental appliances shown in FIG. 1 and FIG. 2 with their light emitting and detecting components having a close alignment and central orientation.

FIG. 5 shows how the close alignment and central orientation of the light source 28 and the PSD 10 can be obtained. A model of the patient's mouth is made when the mouth is set in the fully closed and maximally interdigitated jaw position, which serves as a reference point in studies of jaw movement. A plastic holding device 48 holding the PSD holding box 11 and the light source holder 29 in an optimal position relative to each other is held in position during the making of the upper and lower removeable dental appliances in the dental laboratory process, as shown in FIG. 5.

Figure 6:
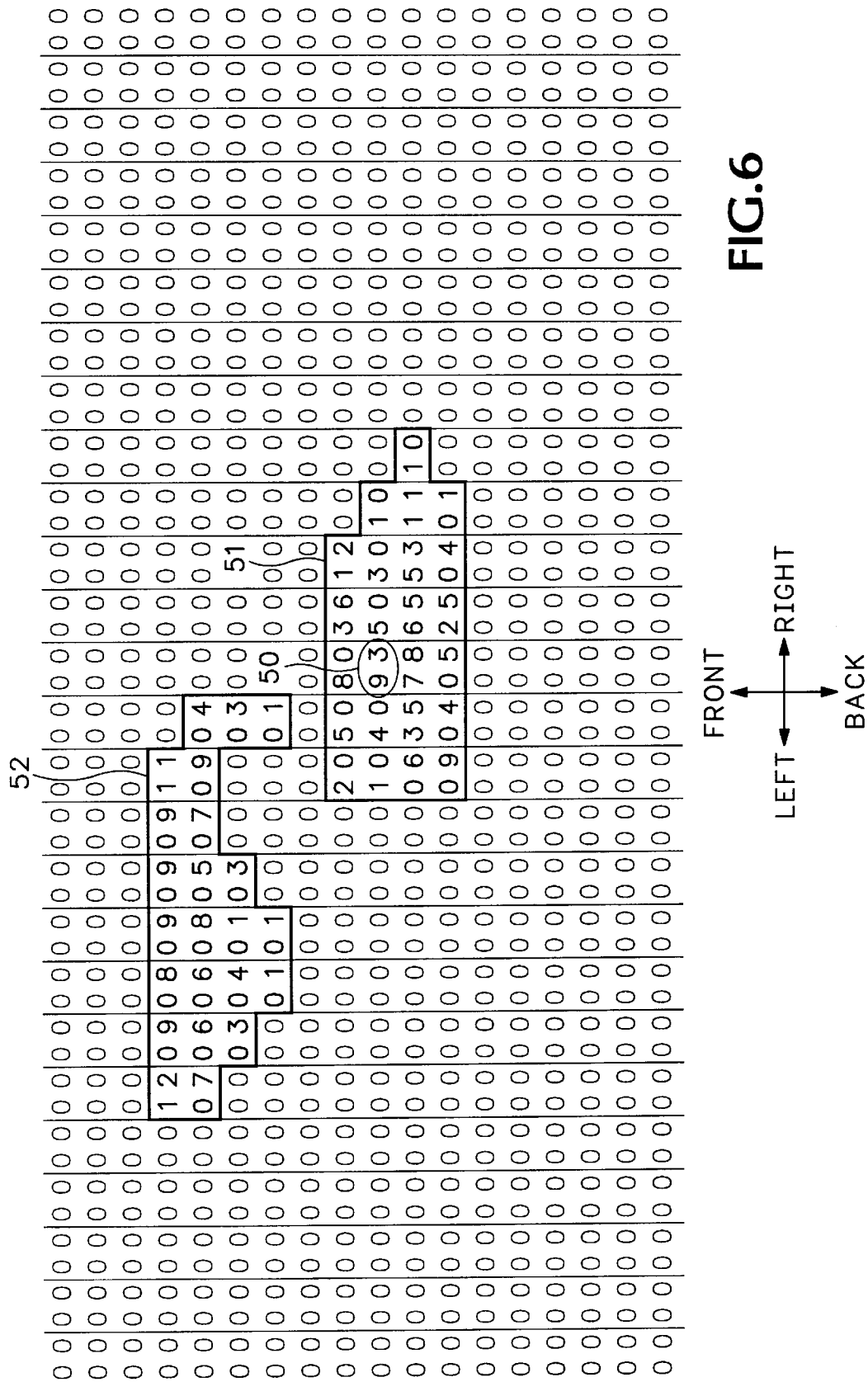
FIG. 6 is an example of the data acquired from two-dimensional analysis of the jaw positions used during clenching and grinding of teeth.

FIG. 6 shows an example of one way of displaying the data acquired from two-dimensional for analysis of the jaw positions used during detecting clenching and grinding of teeth. The center of the coordinates represents the reference position 50 of the lower jawbone, usually taken with the jaw fully closed on the back teeth, known as the intercuspal position. The numbers associated with the coordinates represent the total time, in seconds, where clenching and grinding occurred at that jaw location. For the example in FIG. 6, most of the clenching occurred in an area 51 around the reference position 50 concentrating in an area to the right of the reference position. Most of the grinding occurred in an area 52 with the jaw forward and to the left of the reference position rubbing from the extreme left to almost the midline with the jaw still held forward.

Figure 7:
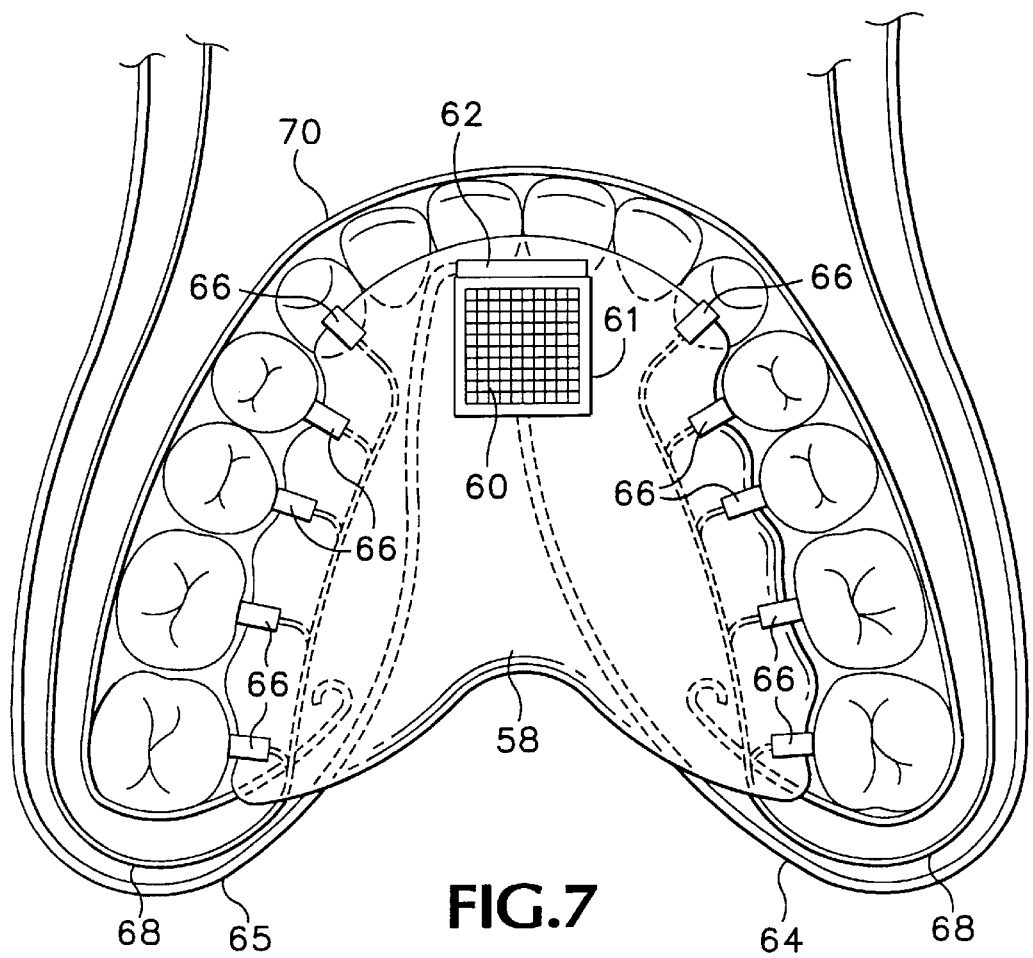
FIG. 7 is a coronal view of the palate and upper dental arch fitted with a removeable dental appliance holding a three dimensional embodiment of the jaw tracking device.

FIG. 7 shows an embodiment of the jaw tracking invention which tracks movement in a vertical plane as well as the horizontal plane. This embodiment is usually employed together with acoustic sensors which are embedded in the same appliance in order to correlate the contacts made by the teeth when closing with the precise pathway of the closing jawbone. Thus this embodiment is used when the patient upright and awake and the information is transmitted by wires rather than by telemetry. The two PSDs 60, 62 have substantially planar, or two-dimensional, detection surfaces that are at substantially right angles to one another. The two PSDs 60, 62 are held in position by a PSD holding box 61 mounted in the acrylic molding 58 of a removable dental appliance held onto the teeth by a stabilizing wire 70. 1D-PSD outputs 65 and 2D-PSD outputs 64 are sent out of the mouth on a coaxial cable. Acoustic sensors 66 are attached to each tooth and held in place by the removable dental appliance. The acoustic sensors 66 are used to relay the order and timing of tooth contacts with each tapping of the jaw. The acoustic sensor outputs 68 are also sent out of the mouth on coaxial cable bundled with the 1D-PSD outputs 65 and 2D-PSD outputs 64.

Figure 8:
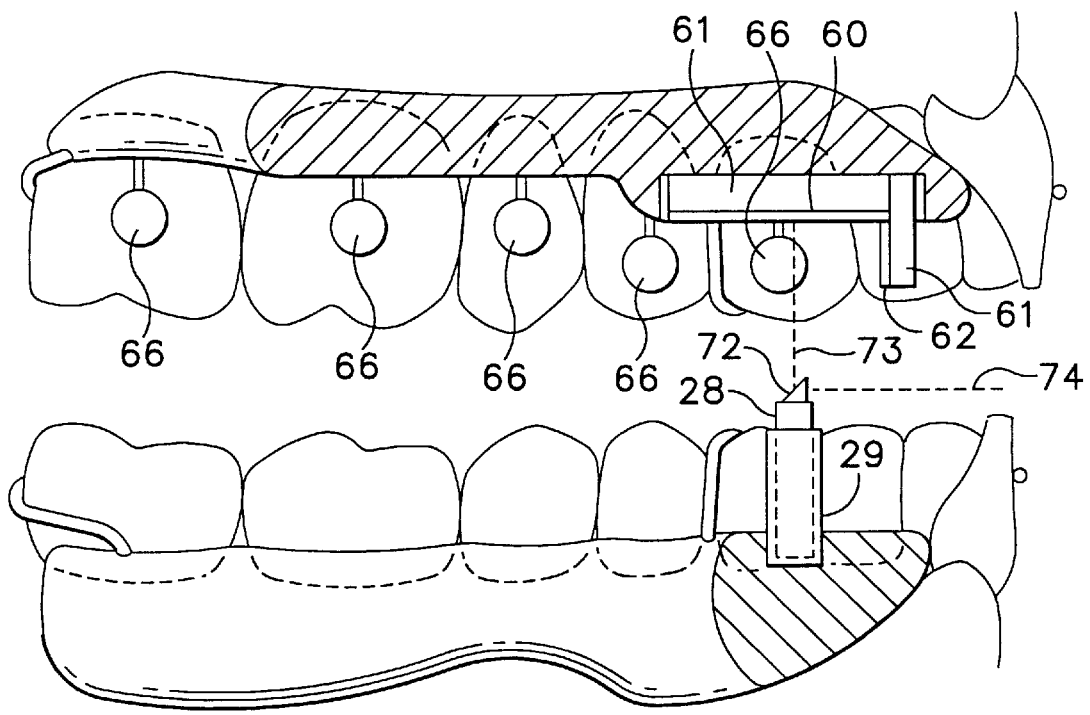
FIG. 8 is a cutaway side view of a partly open mouth using the upper dental appliance of FIG. 7 and a lower dental appliance much like the one illustrated in FIG. 2.

FIG. 8 is a cutaway side view of a partly open mouth with the upper dental appliance of FIG. 7 and the lower dental appliance of FIG. 2. The 2D-PSD 60 and the 1D-PSD 62 are set in the PSD holding box 61 in the upper dental appliance. The light source 28 is set in the light source holder 29 in the lower dental appliance. In the second embodiment, with both the 1D-PSD 62 and the 2D-PSD 60, the light source includes a beam splitter 72, which splits the light into a vertical beam 73 and a horizontal beam 74.

Figure 9:
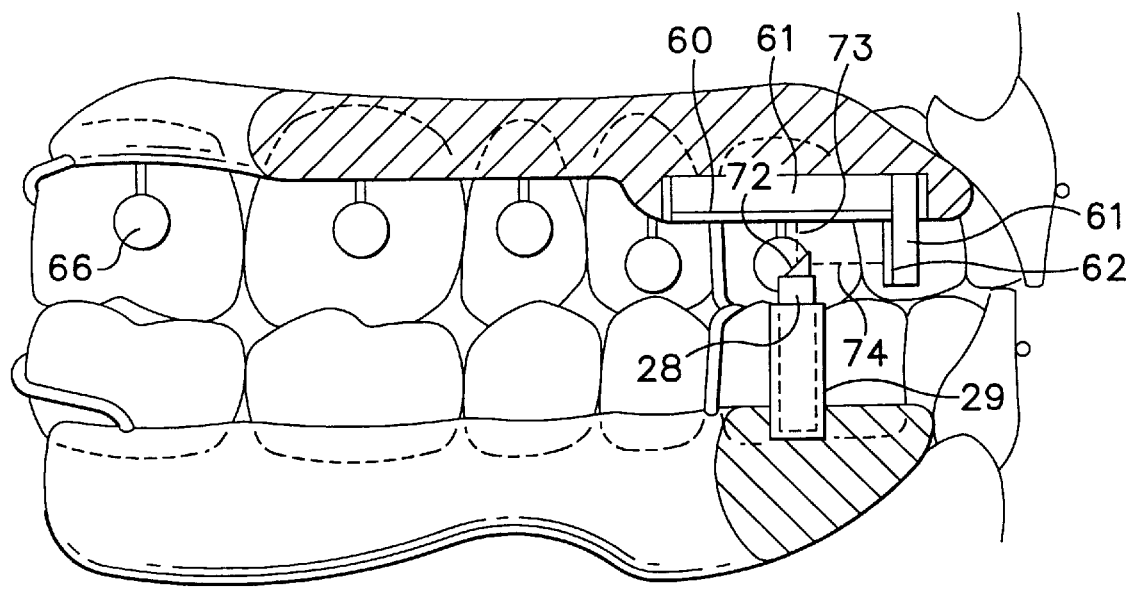
FIG. 9 is a cutaway side view of a closed mouth using the upper dental appliance of FIG. 7 and a lower dental appliance much like the one illustrated in FIG. 2.

FIG. 9 is a cutaway side view of a closed mouth with the upper dental appliance of FIG. 7 and the lower dental appliance of FIG. 2. The vertical beam 73 is projected onto the 2D-PSD 60, while the horizontal beam 74 projects onto the 1D-PSD 62 when the mouth is closed or nearly closed. The acoustic sensors 66 are also shown, tracking the order and timing of tooth contacts with each tapping of the jaw.

Other variations on the invention are possible. For example, the jaw tracking components can be attached directly to the dental arches with temporary cements or dental impression materials rather than embedded in a removable dental appliance.

The construction and operation of the invention will now be described.

To fabricate the removable dental appliances that hold the components of the jaw tracking device, a dentist takes impressions of the patient's teeth to create a stone or gypsum model. A dental laboratory mounts these models in a fully closed and interdigitated position to create the removable dental appliances using the plastic holding device 48 shown in FIG. 5. The plastic holding device 48 holds the PSD holding box 11 and the light source holder 29 in place while forming the removable dental appliances. The light source 28, the single PSD 10 or the 1D-PSD 62 and 2D-PSD 60 combination, and any other necessary hardware are added to the dental appliance before use. In an alternative embodiment, an active pixel sensor may used instead of the position sensitive detector 10.

After the lower and upper dental appliances have been attached to the patient's mouth, a reference position of the lower jawbone is established, usually with the jaw fully closed in the intercuspal position. Displays of the jaw tracking information center on this reference point.

When the invention is used during sleep with telemetry, the outputs from the PSD 10 are routed through an amplifier 12 and signal conditioning element 13 where they are multiplexed at a predetermined periodic rate into a single RF transmitter 15. The signals from the transmitter 15 are received outside of the mouth by an antenna then digitized by an A/D converter and then fed into a computer for display.

When the jaw tracking device is used in conjunction with acoustic sensors (occlusal contact sensors) 66, the patient is requested to open and close the jaw until the teeth tap together. With each tap, information is gathered from the two PSDs 60, 62 and the acoustic sensors 66 from the coaxial cables 68, 64 and 65.

Having described and illustrated the principles of the invention in a preferred embodiment thereof, it should be apparent that the invention can be modified in arrangement and detail without departing from such principles. I claim all modifications and variations coming within the spirit and scope of the following claims.

We claim:

1. A method for tracking a person's lower jaw movement comprising:

mounting a substantially planar light detector adjacent a first dental arch of the person, said detector being received within the person's mouth;

mounting a light source adjacent a second dental arch of the person, said light source being received within the person's mouth and directed toward the sensor;

turning the light on;

sensing the location of light shining on the detector; and communicating the sensed location from inside the person's mouth to outside the person's mouth.

2. The method of claim 1 wherein said method further comprises turning the light on responsive to contact of teeth in the first dental arch with teeth in the second dental arch.

3. The method of claim 1 wherein mounting a substantially planar light detector adjacent a first dental arch of the person comprises installing the detector in a first dental appliance that attaches to teeth in the first dental arch.

4. The method of claim 1 wherein mounting a light source adjacent a second dental arch of the person comprises installing the light source in a second dental appliance that attaches to teeth in the second dental arch.

5. The method of claim 1 wherein said method further comprises generating electrical data that indicates the location of light shining on the detector.

6. The method of claim 5 wherein communicating the sensed location from inside the person's mouth to outside the person's mouth comprises transmitting the data to a receiver outside the person's mouth.

7. The method of claim 5 wherein communicating the sensed location from inside the person's mouth to outside the person's mouth comprises applying the data to a conductor that extends from inside the person's mouth to outside the person's mouth.

8. The method of claim 1 wherein said method further comprises:

mounting a second substantially planar light detector adjacent the first dental arch of the person, said second detector being received within the person's mouth;

mounting a second light source adjacent the second dental arch of the person, said second light source being received within the person's mouth and directed toward the second sensor;

turning the second light on;

sensing the location of light shining on the second detector; and communicating the sensed location of light shining on the second detector from inside the person's mouth to outside the person's mouth.

9. An apparatus for tracking a person's lower jaw movement comprising:

a first dental appliance formed to fit a first dental arch on said person;

a second dental appliance formed to fit a second dental arch on said person;

a light detector mounted on said first dental appliance; and a light source mounted on said second dental appliance, said light source shining on said detector when said appliances are so fitted and said light is on, said detector generating electrical data related to the position of said light on said detector when said apparatus is in operative condition.

10. The apparatus of claim 9 wherein said apparatus further comprises means for communicating said data from the inside of said person's mouth to the outside of said person's mouth.

11. The apparatus of claim 10 wherein said communicating means comprises a conductor.

12. The apparatus of claim 10 wherein said communicating means comprises a transmitter located inside the patients mouth, when said apparatus is in operative condition, and a receiver located outside the patient's mouth.

13. The apparatus of claim 9 wherein said apparatus further comprises a pressure sensitive switch positionable between an upper and lower tooth of the person, said switch being operatively connected to said light source for turning it on responsive to closing said switch.

14. The apparatus of claim 9 wherein said first dental appliance comprises:

a molded portion formed to fit against the person's palate; and a wire portion connected to the molded portion and adapted to anchor the molded portion to teeth in the first dental arch.

15. The apparatus of claim 14 wherein said apparatus further includes a beam splitter for generating said second light source from said first light source.

16. The apparatus of claim 9 wherein said apparatus further comprises:

a second position sensitive detector mounted on said first dental appliance; and a second light source mounted on said second dental appliance, said second light source shining on said second detector when said appliances are so fitted and said second light is on, said second detector generating electrical data related to the position of said second light on said second detector when said apparatus is in operative condition.

17. The apparatus of claim 16 wherein said light detectors include a substantially planar detection surface for sensing light position and wherein said detection surfaces are in different planes relative to one another.

18. The apparatus of claim 17 wherein said detection surfaces are at a substantially right angle relative to one another.

19. The apparatus of claim 9 wherein said light source is a position sensitive detector.

20. The apparatus of claim 9 wherein said light source is an active pixel sensor.

21. An apparatus for tracking a person's lower jaw movement comprising:

a position sensitive detector;

means for mounting the position sensitive detector to a first dental arch on said person;

a light source; and means for mounting the light source to a second dental arch on said person, said light source shining on said detector when said light source is on, said detector generating electrical data related to the position of said light on said detector when said apparatus is in operative condition.

* * * * *